United States Patent
Lomas et al.

(10) Patent No.: US 8,576,980 B2
(45) Date of Patent: Nov. 5, 2013

(54) APPARATUS AND METHOD FOR ACQUIRING SECTIONAL IMAGES

(75) Inventors: David Lomas, Cambridge (GB); Martin J. Graves, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 678 days.

(21) Appl. No.: 12/522,658

(22) PCT Filed: Jan. 10, 2008

(86) PCT No.: PCT/GB2008/000077
§ 371 (c)(1),
(2), (4) Date: Oct. 28, 2009

(87) PCT Pub. No.: WO2008/084232
PCT Pub. Date: Jul. 17, 2008

(65) Prior Publication Data
US 2010/0046695 A1  Feb. 25, 2010

(30) Foreign Application Priority Data
Jan. 10, 2007 (GB) .................................. 0700470.8

(51) Int. Cl.
*A61B 6/03* (2006.01)
*G06K 9/00* (2006.01)

(52) U.S. Cl.
CPC .... *A61B 6/03* (2013.01); *G06K 9/00* (2013.01)
USPC ............... 378/4; 345/154; 345/156; 345/161

(58) Field of Classification Search
CPC ................................... A61B 6/03; G06K 9/00
USPC .............. 378/4; 345/156–184, 419–427, 154; 600/407; 715/700–866
See application file for complete search history.

(56) References Cited

U.S. PATENT DOCUMENTS 4,803,413 A * 2/1989 Kendig et al. ................. 318/648
5,503,040 A * 4/1996 Wright ..................... 74/471 XY (Continued)

FOREIGN PATENT DOCUMENTS

| CN | 1654009 A | 8/2005 |
|---|---|---|
| CN | 1759810 A | 4/2006 |

(Continued)

OTHER PUBLICATIONS

Teistler et al., Virtual Tomography: A New Approach to Efficient Human-Computer Interaction for Medical Imaging, 2003, Proceedings of the SPIE, vol. 5029, pp. 512-519.*

(Continued)

*Primary Examiner* — Toan Ton
*Assistant Examiner* — John Corbett
(74) *Attorney, Agent, or Firm* — Osha Liang LLP

(57) ABSTRACT

Disclosed is a computer implemented method of interrogating volumetric data, the method including the steps of: defining a reference surface relative to the volumetric data; providing an interrogation window lying in a movable interrogation plane intersecting the reference surface and the interrogation window intersecting the volumetric data, said interrogation plane having a pole lying in it about which pole said interrogation plane is rotatable, wherein movement of the interrogation plane provides a corresponding movement of the interrogation window; for each movement of the interrogation plane, determining the point of intersection of said pole and said reference surface, determining the relative angle of rotation of said interrogation plane about said pole and determining the angle of inclination of said pole to said reference surface; and on the basis of said determinations, providing a sectional image through the volumetric data corresponding to the position of the interrogation window within the volumetric data. Also disclosed is a computer system for implementing the method according to any one of the preceding claims, the system includes a processor for performing the steps of the method and a visual display for displaying said sectional image.

21 Claims, 6 Drawing Sheets

(56) References Cited

U.S. PATENT DOCUMENTS

| | | | |
|---|---|---|---|
| 5,701,140 A | | 12/1997 | Rosenberg et al. |
| 6,108,573 A | | 8/2000 | Debbins et al. |
| 6,512,373 B1 | * | 1/2003 | Griffin et al. ............... 324/318 |
| 6,947,584 B1 | * | 9/2005 | Avila et al. .................. 382/131 |
| 7,408,348 B1 | * | 8/2008 | Damadian et al. ........... 324/318 |
| 2003/0109857 A1 | | 6/2003 | Sanchez et al. |
| 2004/0145585 A1 | * | 7/2004 | Fontius ......................... 345/419 |
| 2005/0154292 A1 | | 7/2005 | Tank |
| 2005/0177054 A1 | | 8/2005 | Yi et al. |
| 2007/0032720 A1 | * | 2/2007 | Koivukangas et al. ....... 600/407 |
| 2007/0279436 A1 | | 12/2007 | Ng et al. |
| 2008/0278448 A1 | * | 11/2008 | Nilsagard et al. ............. 345/161 |

FOREIGN PATENT DOCUMENTS

| | | | |
|---|---|---|---|
| EP | 0 365 141 A | | 4/1990 |
| EP | 0 997 851 A2 | | 5/2000 |
| GB | 2347199 A | | 8/2000 |
| JP | 6-203140 A | | 7/1994 |
| JP | 09238915 A | * | 9/1997 |
| JP | 2005-118160 A | | 5/2005 |
| WO | 2004/111826 A1 | | 12/2004 |
| WO | 2006/066401 A1 | | 6/2006 |

OTHER PUBLICATIONS

Teistler et al., Simplifying the Exploration of Volumetric Images: Development of a 3D User Interface for the Radiologist's Workplace, Available online Mar. 27, 2007, Journal of Digital Imaging, vol. 21, Supplement 1, pp. S2-S12.*

Graves et al., Constrained Surface Controllers for Three-dimensional Image Data Reformatting, Jul. 2009, Radiology, vol. 252, No. 1, pp. 218-224.*

Steed et al., 3D Interaction with the Desktop Bat, 1995, Computer Graphics Forum, vol. 14, pp. 97-104.*

PTO 13-1206 which is a for translation Yamagata (JP 9-238915).*

Chinese Office Action for Application No. 200880005130.7, mailed on Feb. 16, 2011 (19 pages).

International Search Report w/translation from PCT/GB2008/000077 dated May 27, 2008 (3 pages).

Stainsby, J.A, et al.; "Integrated Real-time MRI User-Interface"; Proc. Intl. Mag, Reson, Med, 11; 2004; p. 537 (1 page).

Hardy, Christopher J., et al.; "Interactive Coronary MRI"; International Society for Magnetic Resonance in Medicine in 1996; 1998; MRM 40:105-111 (7 pages).

Debbins, Josef P. et al.; "Cardiac Magnetic Resonance Fluoroscopy"; Magnetic Resonance Laboratory; 1996; MRM 36:588-595 (8 pages).

Kerr, Adam B. et al.; "Real-Time Interactive MRI on a Conventional Scanner"; Magnetic Resonance Systems Research Laboratory, Department of Electrical Engineering; 1997; MRM 38:355-367 (13 pages).

Yi, Dingrong et. al., "Intuitive and Efficient Control of Real-Time MRI Scan Plane Using a Six-Degree-of-Freedom Hardware Plane Navigator," Medical Image Computing and Computer-Assisted Intervention MICCAI 2004, vol. 3217, 2004, pp. 430-437 (8 pages).

* cited by examiner

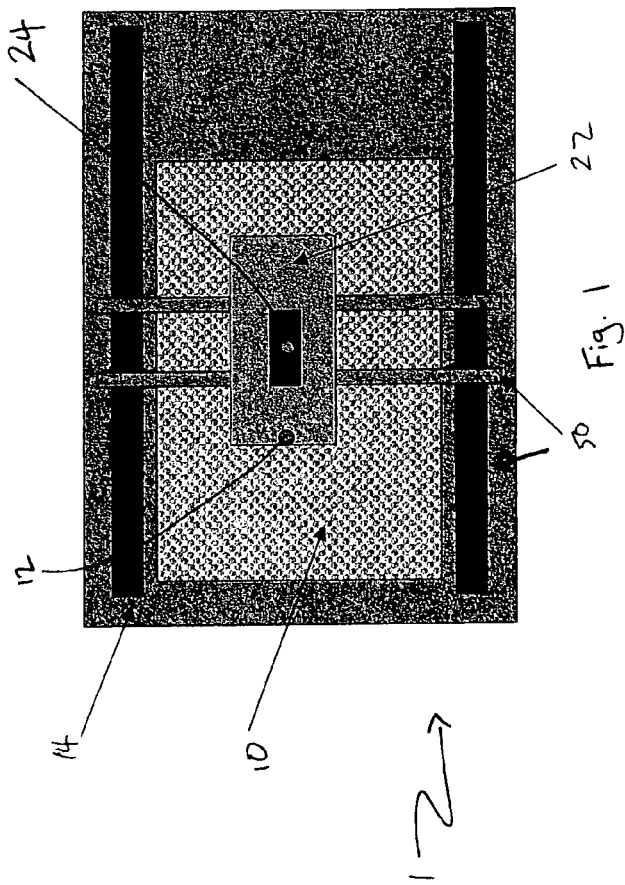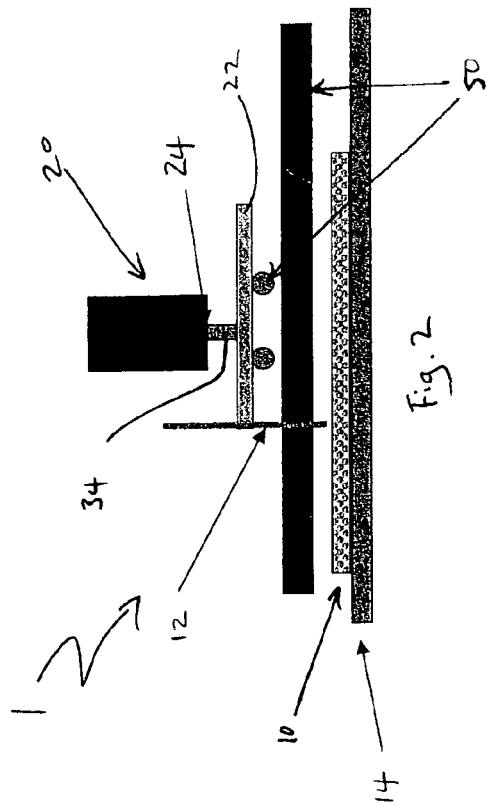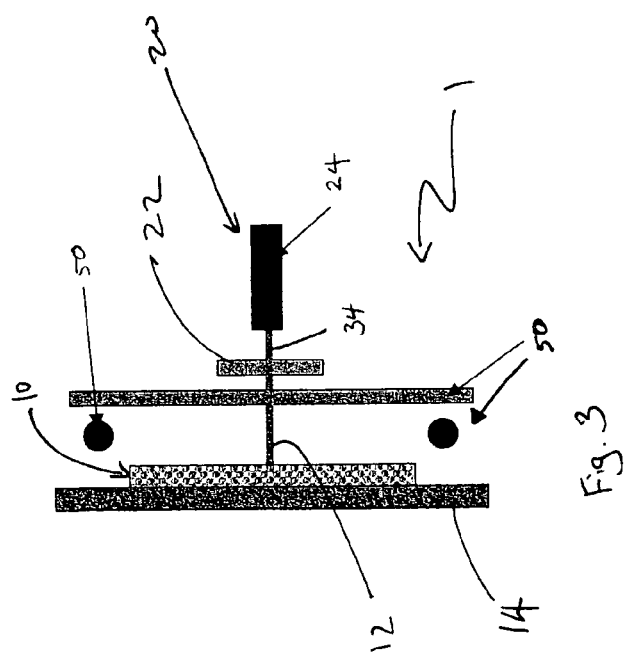

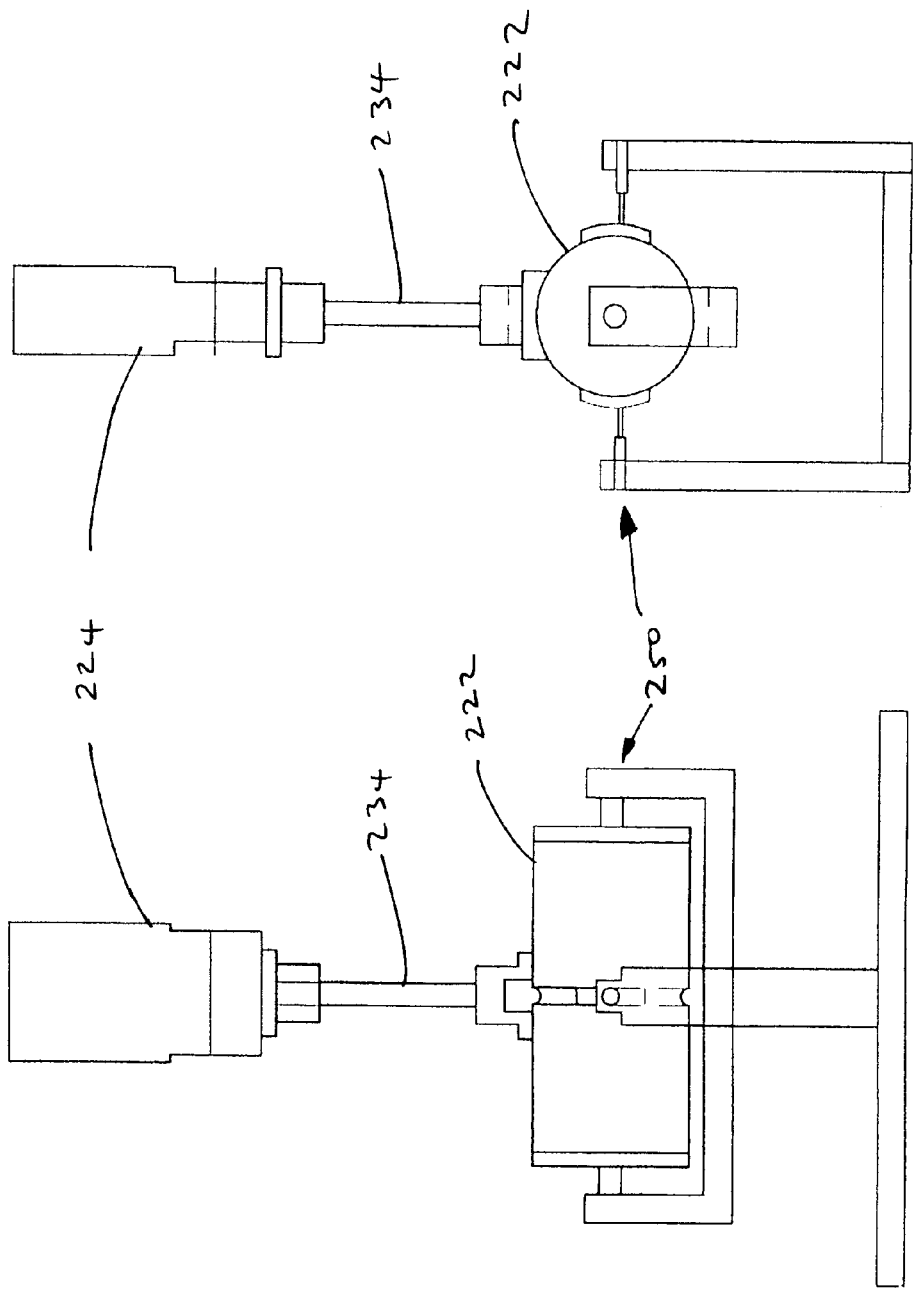

APPARATUS AND METHOD FOR ACQUIRING SECTIONAL IMAGES

The present invention relates to the acquisition of sectional images of a body, either by the interrogation of previously acquired volumetric image data corresponding to the body or by interrogating the body in real-time.

MRI (magnetic resonance imaging) or X-ray CT (X-ray computerised tomography) can be used both to provide sectional views of a body in real-time and to generate volumetric data (i.e. 3D data) corresponding to a body for later interrogation. Often the volumetric data is interrogated to provide displayable sectional views of the body.

The sectional view can be generated anywhere within the volumetric data. Indeed, some systems give the user a sensation that the sectional view can be freely moved (or "navigated") through the volumetric data. However, navigating the sectional view through the volumetric data can prove difficult and disorientating to a user.

For example, in conventional MRI or CT systems, graphical user interface (GUI) interactions allow the user to adjust one or more parameters of the sectional view to navigate the sectional view through the volumetric data. Conventional techniques of adjustment often employ mouse and GUI based methods for determining the location of the image plane containing the sectional view. Examples of techniques include: line drawing (Kerr A B et al., Magn Reson Med 1997; 38; p. 355-367); placing points (Debbins J P et al., Magn Reson Med 1996; 36; p. 588-595); and selecting reference icons (Hardy C J et al., Magn Reson Med 1998; 40; p. 105-111). However, the need for the user to manually adjust these parameters often distracts attention from the displayed sectional view of the volumetric data. This is undesirable when interrogating sectional views of MRI or CT generated volumetric data of e.g. a human subject's body, because abnormalities in the subject's anatomy can easily be overlooked.

In an attempt to overcome the need for the user to divert attention away from the displayed sectional view towards the one or more parameter adjustment GUIs, specialized controllers have been proposed, which allow the user generally to remain focussed on the output image. Such controllers typically provide 6 degrees of freedom (DOF) of image plane control so that the corresponding sectional view remains freely navigatable through the volumetric data. Examples of the 6DOF controllers are the "spaceball" (Hardy C J, et al. Magn Reson Med 1998; 40; p. 105-111), the 3DOF and 6DOF mice (Hardy C J, et al. Magn Reson Med 1998; 40; p. 105-111) and the articulated arm (Stainsby et al., PROC ISMRM 2004: 537).

However, these controllers can rapidly disorientate the user because the image plane (in which the displayed sectional view is generated) is freely movable through the volumetric data. Consequently, a user may have to re-orientate himself in the volumetric data by re-starting the navigation of the image plane from a known location in a known orientation.

It has been proposed that the relative position of the freely movable image plane, in which the sectional view is generated, should be mapped on the volumetric data itself and displayed to the user, thereby providing visual feedback to the user as to the relative position of the image plane with respect to the volumetric data (Hardy C J, et al. Magn Reson Med 1998; 40; p. 105-111 and Stainsby et al., PROC ISMRM 2004: 537). Such feedback is sometimes referred to as image plane tracking. However, the visual feedback still requires the operator to divert attention from the displayed sectional view(s) in order to determine the location of the image plane with respect to the volumetric data. This again creates user distraction, which is undesirable.

The above discussion is mainly directed at the interrogation of volumetric image data. However, the problems associated with navigating volumetric image data using the conventional methods and systems also exist when interrogating a body in real-time, e.g. by MRI or X-ray CT.

Thus, there still remains the problem of how to navigate an image plane through volumetric data (or a body in real-time) in such a way that the user can focus attention on the displayed sectional view whilst maintaining his orientation in the volumetric data (or the body).

In the different diagnostic field of real-time 2D ultrasound scanning, a sectional view of an appropriate subject can be generated and the image plane (containing the sectional view) can be moved freely through the body. However, here the sonographer uses a combination of their knowledge of the subject's internal anatomy and of tactile and spatial cues from the hand manipulating the ultrasound transducer to move the image plane in a controllable, predictable and "automatic" or intuitive way. The sonographer can therefore focus on the sectional view of the subject provided on a display. It is not necessary to use other means, such as mouse/controller/GUIs, in order to establish where the image plane is located in the subject, i.e. image plane tracking feedback is not required.

The present inventors have appreciated that real-time ultrasound has important features lacking in conventional computer implemented data interrogation methods and control systems.

Firstly, the ultrasound transducer motion and the "edge" of the sectional view (in the image plane) are each constrained by a surface, e.g. the skin of the subject. Secondly, the orientation and spatial location of the hand manipulated ultrasound transducer is directly correlated with the displayed sectional view.

These features provide predictability and allow (ultrasound) sonographers to develop and highly refine their coordination so they can concentrate primarily on the output image for diagnostic information and in essence "forget" the transducer movements, which eventually become virtually unconscious actions.

The present invention relates to a method of interrogating volumetric data, e.g. image data, and to a method of controlling an imaging apparatus to acquire a sectional image of a body.

In general terms, the method of interrogating volumetric data includes the steps of: defining a reference surface relative to the volumetric data; providing an interrogation window lying in a movable interrogation plane intersecting the reference surface, the interrogation window intersecting the volumetric data, wherein translation and/or rotation of the interrogation plane provides a corresponding movement of the interrogation window; for each movement of the interrogation plane, determining the relative arrangement of the interrogation window and the reference surface; and on the basis of said determination providing a sectional image through the volumetric data corresponding to the position of the interrogation window within the volumetric data.

In general terms, the method of controlling an imaging apparatus to acquire a sectional image of a body includes the steps of: defining a reference surface corresponding to a control surface which is associated with the body; providing an interrogation window lying in a movable interrogation plane intersecting the reference surface, wherein translation and/or rotation of the interrogation plane provides a corresponding movement of the interrogation window; for each movement of the interrogation plane, determining the mutual arrangement of the interrogation window and the reference surface; and on the basis of said determination providing a sectional image through the body the relative arrangement of the sectional image and the control surface corresponding to the relative arrangement of the interrogation window and the reference surface.

Accordingly, in a first aspect, the present invention provides a computer implemented method of interrogating volumetric data, the method including the steps of:
(i) defining a reference surface relative to the volumetric data;
(ii) providing an interrogation window lying in a movable interrogation plane intersecting the reference surface and the interrogation window intersecting the volumetric data, wherein translation and/or rotation of the interrogation plane provides a corresponding movement of the interrogation window;
(iii) said interrogation plane being associated with a pole about which pole said interrogation plane is rotatable, and for each movement of the interrogation plane, determining the point of intersection of said pole and said reference surface, determining the relative angle of rotation of said interrogation plane about said pole and determining the angle of inclination of said pole to said reference surface; and
(iv) on the basis of said determinations in step (iii), providing a sectional image through the volumetric data corresponding to the position of the interrogation window within the volumetric data.

The determinations in step (iii) are directed at evaluating the relative arrangement of the pole and the reference surface, which ultimately can provide the relative arrangement of the interrogation plane and reference surface. While, alternative mathematical computations and geometrical constructs can be used to arrive at the relative arrangement of the interrogation plane and the reference surface, such computations and constructs may not explicitly determine the relative arrangement of the pole and the reference surface, this information being particularly advantageous when implementing the method in a system and/or together with a controller as described in the aspects below.

Preferably, the pole lies in the interrogation plane.

According to this first aspect, a 2D image plane (i.e. the interrogation plane) is movable through volumetric data, e.g. 3D image data (such as previously acquired MRI volumetric image data or real-time MRI volumetric image data), whilst being constrained to intersect the reference surface.

The reference surface is preferably fixed in position with respect to the volumetric data at least when the interrogation window is being moved by e.g. a user, thereby providing a further safeguard against the user becoming disorientated in the volumetric data.

However, the reference surface (planar or curved) may be movable with respect to the volumetric data during movement of the interrogation plane, e.g. by the user, thereby giving the user the option to move or navigate the interrogation window freely through the volumetric data, and to interrogate the volumetric data accordingly.

A method according to the present invention may include a step of acquiring or generating the volumetric data. For example, where the present invention is used in an MRI or a CT system, the method may include the step of acquiring or generating volumetric data which corresponds to the internal anatomy of a patient.

In another aspect, the present invention provides a computer implemented method of controlling an imaging system to provide a sectional image of a body, the method including the steps of:
(i) defining a reference surface corresponding to a control surface having a pre-determined relationship with the body, with respect to which control surface a sectional image through a particular portion of the body is generatable by the imaging system;
(ii) providing an interrogation window lying in a movable interrogation plane intersecting the reference surface, said interrogation plane having a pole about which pole said interrogation plane is rotatable, wherein movement of the interrogation plane provides a corresponding movement of the interrogation window;
(iii) for each movement of the interrogation plane, determining the point of intersection of said pole and said reference surface, determining the relative angle of rotation of said interrogation plane about said pole and determining the angle of inclination of said pole to said reference surface; and
(iv) on the basis of said pre-determined relationship and said determinations in step (iii), providing a sectional image through the body, the sectional image corresponding to the relative position and orientation of the interrogation window to the reference surface.

The determinations in step (iii) are directed at evaluating the relative arrangement of the pole and the reference surface, which ultimately can provide the relative arrangement of the interrogation plane and reference surface. However, alternative mathematical computations can be used to arrive at the relative arrangement of the interrogation plane and the reference surface. Whilst such computations may not explicitly determine the relative arrangement of the pole and the reference surface, computing the relative arrangement of the interrogation plane and the reference surface is equivalent to such a determination. Indeed, the relative arrangement of the pole and the reference surface is inherently determined in such computations and therefore the alternative computations fall within the scope of the present invention. The reason for explicitly defining such determinations is that it is advantageous to do so when implementing the method in a system and/or together with a controller as described in the aspects below.

In this aspect, the present invention is particularly suited to real-time MRI or CT, and the method may not include a step of acquiring volumetric data—although this is not precluded. Rather, the user can effectively navigate the sectional image directly through a body, for example a human subject's body, whilst the body is in situ e.g. in the MRI or CT system.

The following optional features relate to all of the above aspects.

The reference surface may be planar, but other forms of reference surface may be provided. The reference surface may be curved, for example at least a portion of a sphere, e.g. a hemisphere or a portion thereof, or it may be at least a portion of a cylinder. Preferably, a curved reference surface at least partially surrounds at least a portion of the volumetric data.

The size of the interrogation window, e.g. with respect to the volumetric data, may be adjustable. The resolution of the sectional image, e.g. corresponding to the position of the interrogation window in the volumetric data, may also be adjustable. The location of the interrogation window within the interrogation plane may be adjustable, e.g. to adjust the relative distance between the interrogation window and the reference surface and/or a point in the volumetric data.

Where the reference surface is planar, the pole (or axis) about which the interrogation plane is rotatable is preferably maintained at a constant, e.g. predetermined, angle to the line of intersection of the interrogation plane and the reference surface. It is preferred that the pole is substantially perpendicular to the line of intersection of the interrogation plane and the reference surface. However, the angle between the pole and the line of intersection may be adjustable. For example, the pole may be able to lean (conceptually "within" the interrogation plane) about a lean axis—the lean axis thus being normal both to the pole and to the line of intersection of the interrogation plane and the reference plane, and the lean axis passing through the point of intersection of the pole and the reference surface. Maneuvering the pole about the lean axis provides the user with the sensation that the interrogation window can be "swept" in the interrogation plane.

Where the reference surface is curved, the pole (or axis) about which the interrogation plane is rotatable may be maintained at a constant, e.g. predetermined, angle to a tangent to the reference surface at the point of intersection of the pole and the curved reference surface, the tangent being the tangent which lies in the interrogation plane. This predetermined angle may be a right angle, or substantially a right angle. However, the angle between the pole and this tangent may be adjustable so that the pole can lean (conceptually "within" the interrogation plane) about a lean axis—the lean axis thus being normal both to the pole and to the tangent and passing through the point of intersection of the pole and the curved reference surface. Maneuvering the pole about the lean axis provides the user with a sensation that the interrogation window can be "swept" in the interrogation plane.

Therefore, whether the reference surface is planar or curved, the interrogation plane (and therefore the interrogation window) may have three degrees of rotational freedom, and the interrogation plane may have 5DOF overall: three degrees of rotational freedom and two degrees of translational freedom across the reference surface.

However, the interrogation plane (and therefore the interrogation window) may only have two degrees of rotational freedom, and therefore the interrogation plane may only have 4DOF overall: two degrees of rotational freedom and two degrees of translational freedom across the reference surface.

Where a curved reference surface is at least a portion of a sphere, the pole is preferably constrained to pass through the origin of the spherically curved reference surface (by origin it is meant the point in space which is equidistant to all points on the surface of the spherically curved surface). Therefore, the pole may form a right angle with all the tangents to the point of intersection of the pole and the reference surface. However, it is preferred that the pole certainly forms a right angle with at least the tangent lying in the interrogation plane.

The pole may be able to lean about a lean axis which passes through the point of intersection of the pole and the reference surface.

Having obtained the sectional image, it may be displayed or stored e.g. for future display.

In another aspect, the present invention provides a computer system for implementing a method according to the above aspects, the system including: a processor for performing the steps of the method; and a visual display for displaying the sectional image.

Preferably, the system also includes a controller for maneuvering the interrogation plane with respect to the reference surface. The controller may include a controller body.

The controller may define a constraint surface which corresponds (e.g. which relates in a known way) to the reference surface defined by the computer. Therefore, where the reference surface is planar, the constraint surface is preferably also planar; likewise, where the reference is curved, the constraint surface is preferably curved similarly to the reference surface. However, the reference surface and the constraint surface may not be identical. For example, they may be of similar shape but scaled up or down in size with respect to each other.

Preferably, the controller body is constrained to translate only across the constraint surface. Therefore, the controller may be constrained to have only 5DOF or less, preferably 4DOF, so that the controller body cannot translate in a direction normal to the constraint surface local to the controller body. Translating the controller body across the constraint surface provides in use a corresponding translation of the interrogation plane (and therefore the interrogation window) with respect to the reference surface, whereby the user perceives a correlation between the relative position of the controller body and the constraint surface and the corresponding relative position of the interrogation plane and the reference surface.

Thus, the user can intuitively move, e.g. translate or rotate, the interrogation plane (and therefore the interrogation window) through the volumetric data (by simply moving the controller body with respect to the constraint surface) to display respective sectional images of the volumetric data without having to direct attention away from the sectional images themselves.

In other words, the user intuitively relates the constrained motion of the interrogation plane across the reference surface in a virtual space with the constrained motion of the controller body in real space. The constraint provides the user with directly correlated spatial and orientation control information.

Therefore, the present invention provides an intuitive method of navigating volumetric image data (such as that generated by MRI and CT) allowing the operator to concentrate visually on the displayed sectional images without becoming disorientated or distracted by other interactions, such as having to use separate mouse driven GUIs or having to rely on positional feedback from a 3D reference data displaying image plane tracking.

Nonetheless, an auxiliary image (in addition to the display of the main sectional image) may be displayed to the user, so that the user can determine where the reference surface is in relation to the volumetric data, e.g. prior to beginning the interrogation of the volumetric data.

Preferably, the controller body is rotatable about a rotation axis corresponding to the pole about which the interrogation plane is rotatable, whereby rotation of the controller body about its rotation axis provides a corresponding rotation of the interrogation plane about the pole. The rotation axis may lie within the controller body.

Thus, the user perceives a correlation between the (angular) orientation of the controller body about its rotation axis and the (angular) orientation of the interrogation plane about its (rotation) pole. Therefore, the user can intuitively rotate the interrogation plane (and therefore the interrogation window) about its (rotation) pole in the volumetric data (by simply rotating the controller body) to display sectional images without having to direct attention away from the sectional images. The correlation between this rotational degree of freedom of the interrogation plane and the rotational degree of freedom of the controller body further enhances the ease with which the user can interrogate volumetric data. Indeed, the correlation further safeguards against the user becoming disorientated.

Preferably, the controller body is tiltable about a tilt axis. When both the constraint surface and the reference surface are planar, the tilt axis may correspond to the line of intersection of the interrogation plane and the reference surface discussed above. Where both the constraint surface and the reference surface are curved, the tilt axis may correspond to the tangent to the reference surface at the point of intersection of the pole and the reference surface which lies in the interrogation plane, as discussed above.

Tilting of the controller about the tilt axis provides in use a corresponding change in the angle of inclination of the pole to the reference plane. Thus, the user perceives a correlation between the (angle of) tilt of the controller body with respect to the constraint surface and the angle of tilt of the pole with respect to the reference surface.

Therefore, the user can intuitively adjust the angle of tilt of the interrogation plane (and therefore the interrogation window) with respect to the reference surface and therefore the volumetric data (by simply adjusting the angle of tilt of the controller body with respect to the constraint surface) to display sectional images without having to direct attention away from the sectional images. Indeed, the correlation between the tilt of the controller body and the inclination of the pole further safeguards against a user's becoming disorientated when interrogating volumetric data.

The controller body may also be sweepable about a sweep axis, corresponding in use to the lean axis of the pole. The controller body may be sweepable about the sweep axis to vary the angle between the pole and the tangent discussed above.

As the user manipulates or maneuvers the controller body about and/or across the constraint surface, the position and orientation of the controller body is provided to a computer which is configured to implement the method of the present invention. The computer uses orientation and position information supplied by the controller to determine the corresponding orientation and position of the interrogation plane with respect to the reference surface, whilst e.g. allowing for any scaling factors. Thus, the operator senses (e.g. non-visually) the orientation of and the position of the interrogation plane with respect to the reference surface (and within the volumetric data) by sensing with their hand the corresponding position of the controller body in relation to the constraint surface.

Thus, the present invention provides an intuitive and easy to use controller for navigating volumetric image data (such as from MRI and CT or as part of an interactive real-time MRI system) allowing the operator to concentrate visually on the displayed sectional image without disorientation or distraction by separate interactions such as using mouse driven GUIs or relying on positional feedback from a 3D reference data display. The present invention allows for non-visual senses to be used by the user to obtain the required orientation and position feedback. The correspondence between the constrained controller body (and its constraint with respect to the constraint surface) and the constrained interrogation plane (and its constraint with respect to the reference surface) provides this non-visual feedback.

Preferably, the controller is configured such that the controller body maintains its position when the user removes his hand from it.

The present invention also provides for a system which allows a user to interrogate a body, e.g. by MRI or CT, in real-time. For example, information about the position and orientation of the controller body can be supplied to a computer by the controller. Using this information, the system can then provide a sectional image of the body relative to a control point or surface corresponding to the mutual arrangement of the controller body and constraint surface, which determines the mutual arrangement of the interrogation plane and reference surface.

In another aspect, the present invention provides a controller for use in a part of a system according to the preceding aspect. The controller may include a controller body as previously described. The controller may also include an orientation sensor, for example a magnetic field sensor, to detect the orientation of the controller body, e.g. with respect to the Earth's magnetic field. However, the orientation sensor may include an optical sensor for determining the orientation of the controller body. The controller or controller body may include 1, 2, 3 or more orientation sensors.

The constraint surface may be a physical surface which forms a portion of the controller. Alternatively, the controller may be configured to limit the translation of the controller body such that it translates across a surface which is not a physical surface forming a part of the controller albeit that the constraint surface is a surface in real space. For example, the controller body may be constrained to be translatable across a constraint surface offset in space from a physical surface. The controller body may be constrained to be movable about an origin to sweep out a spherically curved constraint surface or a cylindrically curved constraint surface, or a portion thereof such as a hemispherical or hemicylindrical constraint surface. Such a "swept out" surface may be the constraint surface even though it is not a physical surface.

An orientation sensor may be provided to determine the extent of tilt of the controller body with respect to a predetermined arrangement and/or with respect to the constraint surface. The same orientation sensor, or an additional or alternative orientation sensor, may be provided to determine the extent of sweep of the controller. Such an orientation sensor is preferably included in a controller having a curved, preferably spherical, constraint surface.

The present invention will now be described in more detail by way of example only, with reference to the accompanying figures, in which:

FIG. 1 shows a plan view of a controller according to the present invention;

FIG. 2 shows a side view of a controller according to the present invention;

FIG. 3 shows a front view of a controller according to the present invention;

FIG. 8 shows a side view of a preferred controller according to the present invention;

FIG. 9 shows an end view of the same preferred controller according to the present invention.

Figure 4:
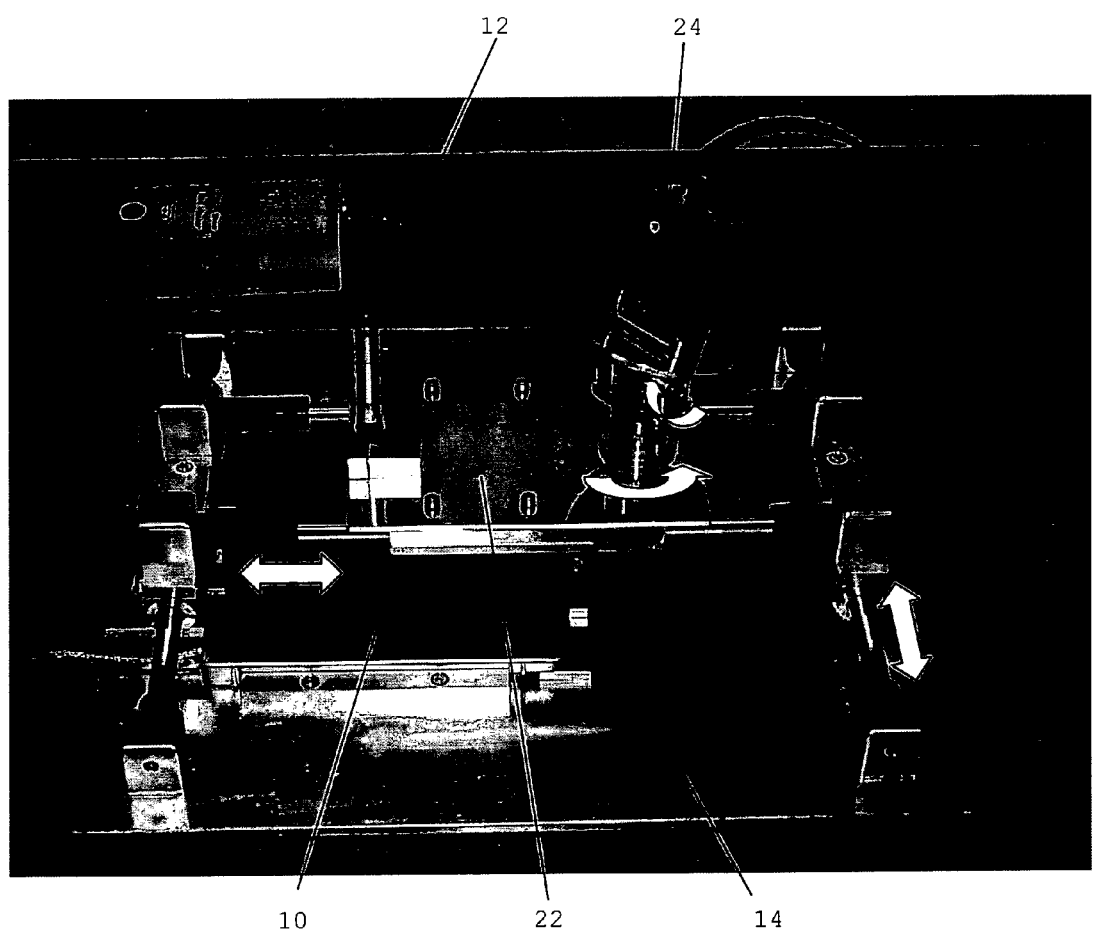
FIG. 4 is an image of a working prototype of the controller of FIGS. 1 to 3.

A computer can be used to generate sectional images (e.g. on a visual display unit) of volumetric data, e.g. acquired by or generated as a result of MRI or X-ray CT, to allow a user to interrogate the volumetric data. The present invention requires that the plane, in which the or each sectional image lies, intersects a pre-determined reference surface. The reference surface may lie proximate to the volumetric data, or it may lie in the volumetric data. The reference surface is preferably planar, but it could be a curved surface, e.g. a spherically curved surface.

The computer provides an image (or interrogation) window which lies in an interrogation plane. When the interrogation window at least partly lies within the volumetric data, the computer may provide a sectional image through the volumetric data corresponding to the interrogation window's position within the volumetric data.

The interrogation plane is preferably movable with respect both to the volumetric data and to the reference surface, although the interrogation plane is required to intersect the reference plane (it is also conceivable that the interrogation plane could lie completely within the reference surface, e.g. where the reference surface is planar, and so it is intended that by intersect, coexistence is also meant). Movement of the interrogation plane produces a corresponding movement of the interrogation window.

A pole may intersect or extend parallel to the interrogation plane, but it preferably lies in the interrogation plane. The interrogation plane, and therefore the interrogation window is rotatable about the pole to provide different sectional images of the volumetric data. The pole (and therefore the interrogation plane and window) is tiltable with respect to the reference surface thereby varying the angle between the pole and the reference surface to provide different sectional images of the volumetric data. Indeed, the point of intersection of the pole and the reference surface is translatable across the reference surface (and therefore the interrogation plane and window are translatable with respect to the reference surface) to provide different sectional images of the volumetric data.

For each movement of the interrogation plane, e.g. by a user controlling the interrogation plane to move, the computer determines the new position of the interrogation window and therefore can provide a new sectional image through the volumetric data, corresponding to the position of the interrogation window in the volumetric data.

The reference surface is in a predetermined position relative to the volumetric data, and the interrogation plane intersects the reference surface. So, the position of the interrogation plane relative to the volumetric data can be determined by the arrangement of the interrogation plane and the reference surface. Therefore, the extent of rotation of the interrogation plane about the pole is determined, the point of intersection of the reference surface and the pole is determined and the angle of inclination of the pole to the reference surface is determined, thereby determining the mutual arrangement of the interrogation plane and the reference surface. Once this arrangement is determined the computer can generate a new sectional image for display on e.g. a visual display unit.

Even if the reference surface is movable with respect to the volumetric data, the computer can determine the (changing) relationship between the reference surface and the volumetric data and determine the position of the interrogation window accordingly and therefore determine the position of the interrogation window with respect to the volumetric data and generate a sectional image of the volumetric data if appropriate. However, the interrogation plane may only have 5DOF with respect to the reference surface such that the interrogation plane is not controllable to translate in a direction normal to the point of intersection of the pole and reference surface, e.g. normal to the reference surface. Preferably, the interrogation plane only has 4DOFs with respect to the reference surface, i.e. two degrees of translational freedom across the reference surface, and two degrees of rotational freedom.

Whilst the above description is directed to the interrogation of volumetric data, e.g. volumetric image data acquired by MRI or X-ray CT of a body, the present invention is also suitable for real-time MRI or X-ray CT.

For example, a computer may implement a method according to the present invention to control an imaging system to generate sectional images of a body. Under the control of a computer, the imaging system may be capable of generating a sectional image arbitrarily through the body, with respect to a control surface (e.g. acting as a reference frame) which has a pre-determined relationship with the body. The computer may define a reference surface corresponding to the control surface and it may define an interrogation plane and window as above, thereby providing the user with the advantages outlined above.

In response to a movement of the interrogation window relative to the reference surface e.g. by a user, the imaging system may generate a sectional image of the body in a portion of the body relative to the control surface corresponding to the position and orientation of the interrogation window relative to the reference surface.

FIGS. 1, 2 and 3 respectively show a controller 1, according to the present invention, for maneuvering the interrogation plane with respect to the reference surface. The controller 1 provides a physical equivalent of the interrogation plane and reference surface generated by the computer (albeit scaled up or down in size as desired). The controller is shown in more detail in FIG. 4, which is an image of a working prototype. The arrows in FIG. 4 indicate the motions allowed by the controller.

The controller 1 includes a graphics tablet 10 and a graphics pen 12 for use with the tablet 10. The pen 12 and the tablet 10 are arranged so that the pen 12 can translate across the surface of the tablet 10 thereby producing in use an output signal from the tablet 10 indicating the position of (the tip of) the pen 12 on or proximate to the surface of the tablet 10. The tablet 10 provides a planar surface which corresponds to a constraint surface, which itself corresponds in use to the reference surface provided by the computer. The surface of the tablet 10 across which the pen translates may be employed as the constraint surface. However, in the present embodiment the constraint surface which corresponds in use to the reference surface is a surface offset from the surface of the tablet 10. The tablet 10 may be mounted on a base plate 14, which may be formed of metal e.g. aluminium, to provide mechanical stability.

Figure 5:
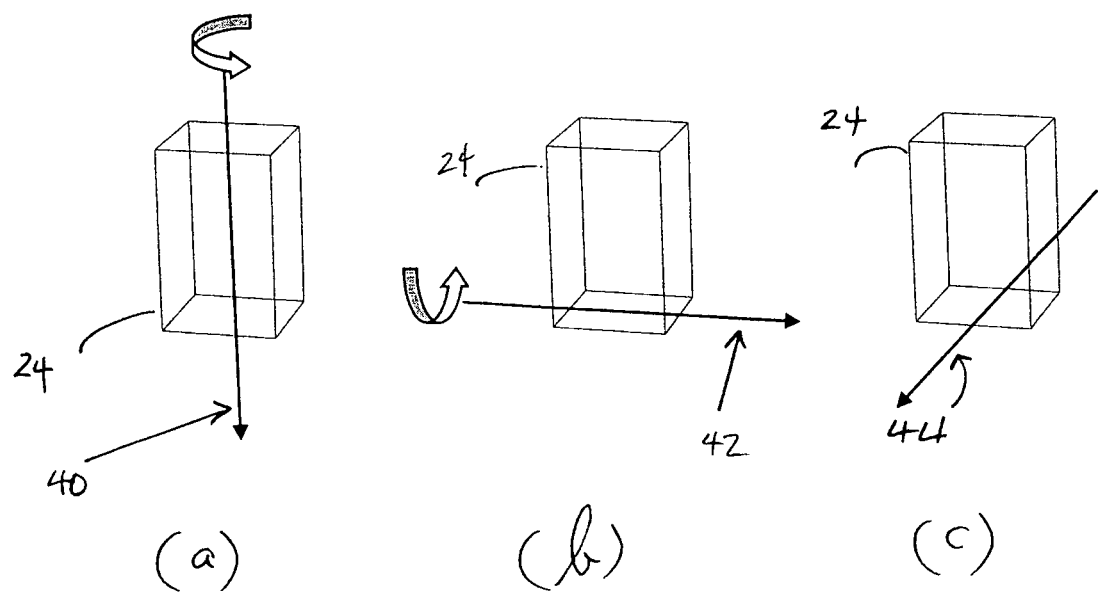
FIG. 5 shows schematic views of a handle and its associated axes of rotation where (a) shows the axis of rotation, (b) shows the axis of tilt and (c) shows the axis of lean of the handle.

The controller 1 includes a controller body 20 having a handle 24 movably coupled to a stage 22. The handle 24 is preferably movably coupled to (or mounted on) the stage 22 so that with respect to the stage 22 the handle 24 only has two degrees of freedom (2DOF), namely rotation about a rotation axis 40 and flexion (or tilt) about a flex (or tilt) axis 42. FIGS. 5a and 5b respectively schematically show the rotation axis 40 and tilt axis 42 of the handle 24. However, the handle 24 may have another degree of freedom relative to the stage 22, namely lean, as discussed below.

The rotation axis 40 of the handle 24 corresponds to the pole of the interrogation plane. So, where the handle is rotated about the rotation axis 40, e.g. by 30°, the interrogation plane is rotated about the pole to a corresponding extent, e.g. 30°. Likewise, tilting the handle 24 about its tilt axis 42 produces a corresponding inclination of the pole (and therefore the interrogation plane) to the reference surface.

Coupling of the handle 24 and the stage 22 by a jointed and/or hinged stem 34 allows the handle 24 to be tilted and rotated with respect to the constraint surface, about respective axes. The handle may have an extent of flex, or tilt, of 180° with respect to the constraint surface, but other tilt ranges could be provided. Preferably, the controller body can rotate about the rotation axis 40 by at least 360°.

Preferably, the rotation axis 40 of the handle 24 is located within the handle as shown in FIG. 5a, but it may not. The tilt axis 42 may also be located within the handle. Alternatively, the tilt axis 42 may lie outside the handle. Preferably, the tilt axis is located at an edge of the handle 24, as shown in FIG. 5b.

The combination of tilt axis 42 and rotation axis 40 permits the user to arrange the rotation axis 40 of the handle 24 at any oblique angle to (or to be perpendicular to) the constraint surface, and the computer can determine a corresponding arrangement of the pole lying within the interrogation plane and the reference surface, in order to be able to display a sectional image corresponding to the position of the interrogation window within the interrogation plane.

Furthermore, a frame 50 has a set of X-Y guides, on which the stage 22 is mounted to be freely slidable in a plane corresponding to the constraint plane. The X-Y guides allow the stage 22 to translate over the surface of the tablet 10. The pen 12 attached to the stage 22 is therefore translatable across the surface of the tablet 10.

In the preferred embodiment, the handle 24 is fixed so as not to be rotatable about the lean axis 44 shown in FIG. 5c (i.e. the handle 24 is not leanable about the lean axis 44). The handle therefore has 4DOF: rotation about the rotation axis 40; tilt about the tilt axis 42; and translation in a plane (e.g. parallel to the constraint surface) providing two further degrees of freedom. However, in another embodiment the handle 24 may be leanable about the lean axis 44, thereby providing a handle with 5DOF.

The rotation axis 40 of the handle 24 is positionable at any point on the constraint surface, thereby allowing the rotation axis 40 to be arrangeable at any oblique angle (or normal) to the constraint surface at any point on the constraint surface. Further, translating the handle 24 with respect to the tablet 10 produces a corresponding translation of the rotation axis 40 with the constraint surface, and the computer provides a corresponding translation of the pole with respect to the reference surface. The computer can therefore determine a corresponding arrangement of the pole of the interrogation plane and the reference surface.

To determine the orientation of the rotation axis 40 with respect to the constraint surface, and to determine the extent of rotation of the handle 24 about the rotation axis 40, the controller 1 includes an orientation sensor. The orientation sensor may be included in the handle 24 itself. Preferably, an MTi orientation sensor (Xsens technologies BV, Holland) is mounted within the handle. Such an orientation sensor senses the local magnetic field and provides a signal which indicates the orientation of the sensor (and therefore the handle 24) in the magnetic field. In the preferred embodiment, the quaternion output of the MTi orientation sensor is used to obtain the orientation of the controller body (to avoid gimbal lock).

The respective outputs of the tablet 10 (providing a relative 2D position on a surface corresponding to the constraint surface) and the orientation sensor can be interfaced through their respective drivers on the computer. The arrangement of the handle 24 and its rotation axis 40 with respect to the constraint surface can therefore be determined by the computer as being intersecting planes or surfaces.

A user's movement of the handle 24 with respect to the constraint surface is determined and the interrogation plane is moved with respect to the reference surface in a corresponding way. The computer determines the location of the interrogation window in the volumetric data, and a sectional image can be generated.

Constraining the interrogation plane to intersect the reference surface allows the rapid location of complex oblique planes in previously acquired volumetric data sets (obtained by e.g. 3D T1 weighted MRI or multi-detector helical X-ray CT) corresponding to the mutual arrangement of the handle 24 and the constraint surface. Therefore, a user wishing to interrogate volumetric image data can easily navigate the interrogation plane through the data without becoming disorientated.

The interrogation window is preferably provided in the interrogation plane, but it may be provided offset from the interrogation plane.

The controller can also be interfaced to an MRI system whereby the controller provides the geometry coordinates for the interrogation window in such a way that the MRI system obtains a 2D image at the corresponding location within the magnet bore in which a subject is positioned. By using fast acquisition methods such as balanced or spoiled gradient echo sequences, for example, real-time MRI is possible and the controller permits the interactive positioning of the interrogation window within the subject to acquire a sectional image. It is also possible that the controller could be interfaced to a CT system, e.g. an X-ray CT system.

The present invention has been used to perform real-time MRI image navigation in a human volunteer without the operator becoming disorientated or needing to displace visual attention from the output image. The controllers shown in FIG. 4 and FIGS. 10a and b (discussed below) were both successfully used for real-time MRI image navigation and control.

Figure 7:
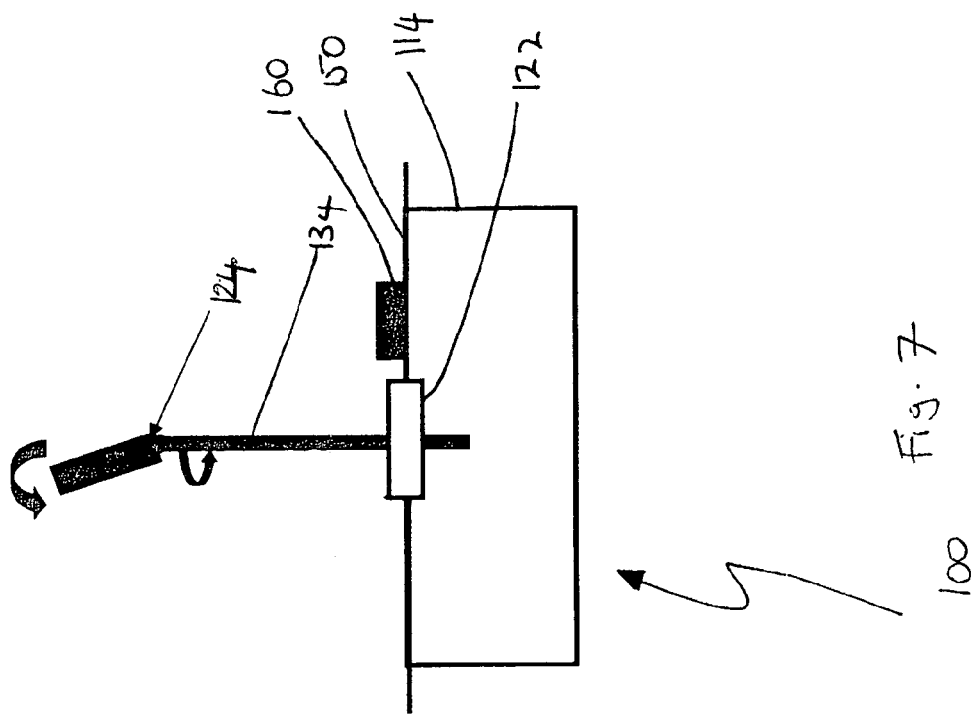
FIG. 7 shows a side view of the same alternative controller according to the present invention.
Figure 6:
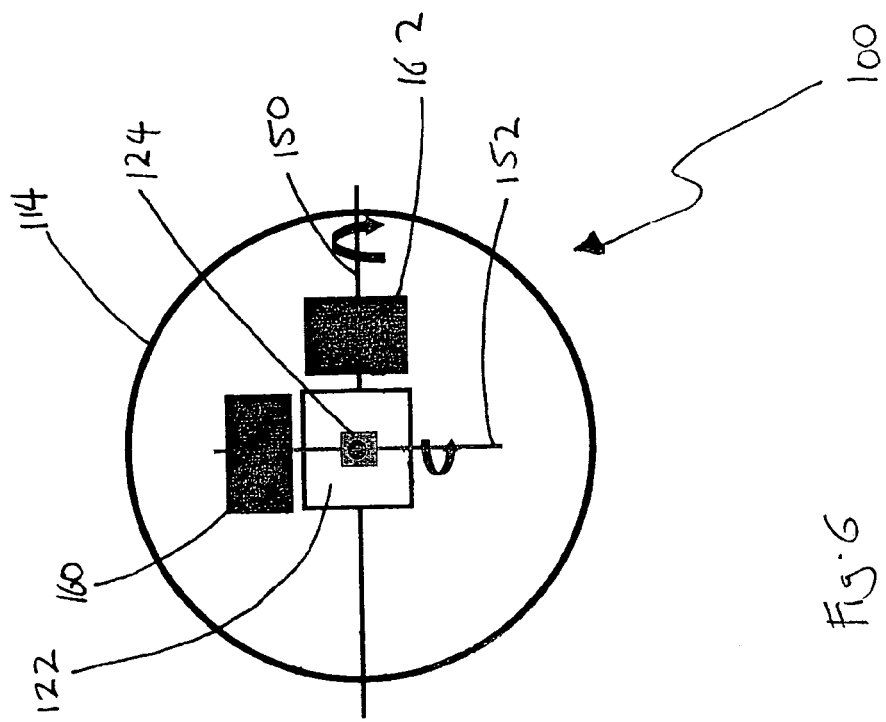
FIG. 6 shows a plan view of an alternative controller according to the present invention.

A controller 100 according to the present invention is shown in FIGS. 6 and 7. The controller 100 includes a handle 124 similar to the handle 24 described above. The handle 124 is movably coupled to a stage 122, preferably by a jointed or hinged stem 134 similar to the stem 34 described above.

The handle 124 is rotatable about a rotation axis 40 corresponding in use to the pole lying in the interrogation plane, and it is tiltable about a tilt axis 42, where the tilt corresponds in use to the inclination of the pole (lying in the interrogation plane) relative to the reference surface. The handle 124 may be leanable about a lean axis 44.

The stage 122 is connected to a base 114 by axle rods 150 and 152. The stage 122 (and therefore the handle 124 coupled to the stage 122 by the stem 134) is preferably articulatable about the respective axle rods, e.g. by means of a two axis gimbal mounting. The stage 122 is preferably not translatable. Therefore, the handle can be articulated about a centre of rotation, provided by the respective axle rods, to be translatable across a curved surface (e.g. a spherically curved surface, such as a hemisphere or a portion thereof) which acts as the constraint surface. The curved surface across which the handle is translatable may not be a physical surface even though it is a surface in real space. Nonetheless, the curved surface corresponds in use to the reference surface.

Therefore, articulating the handle about the centre of rotation of the constraint surface (e.g. the origin of the spherically curved surface) provides in use a corresponding articulation of the pole lying in the interrogation plane about the origin of the correspondingly spherically curved reference surface.

Further, the rotation axis 40 (corresponding in use to the pole lying in the interrogation plane) can be arranged at any angle to the curved constraint surface.

The controller 100 includes an orientation sensing assembly to determine the orientation of the handle 124. The orientation sensing assembly may include an orientation sensor for determining the orientation of the handle 124 similarly to the controller 1 described above. The orientation sensor may be included in the handle. The orientation sensor may include a magnetic field sensor or an optical sensor as described above.

To determine the position and orientation of the handle 124 with respect to the constraint surface, the orientation assembly may further include detectors 160, 162 for determining the extent of rotation of the handle 124 about the centre of rotation or articulation of the curved constraint surface. In the preferred embodiment, an orientation sensor is provided for each axle rod, to determine the extent of rotation of the respective axle rod. By collating the orientation of the handle and the respective orientations of the axle rods, the position and orientation of the rotation axis 40 of the handle 124 on the constraint surface can be determined.

FIGS. 8 and 9 show an alternative preferred embodiment of a controller according to the present invention. A handle 224 is rotatably mounted on a rod 234 to a body 222 which is rotatable in a structure 250 about orthogonal axes to permit the handle to translate over a curved constraint surface e.g. a hemispherical surface. The structure 250 may have two gimbals for rotation about the orthogonal axes. The body 222 preferably includes an orientation sensor as previously described allowing the position of the handle to be determined with respect to the constraint surface.

Combining this position with the orientation of the handle 224 (preferably provided by an orientation sensor included in the handle) allows the orientation and position of the rotation axis 40 of the handle 224 with respect to the e.g. curved constraint surface to be determined.

Figure 10:
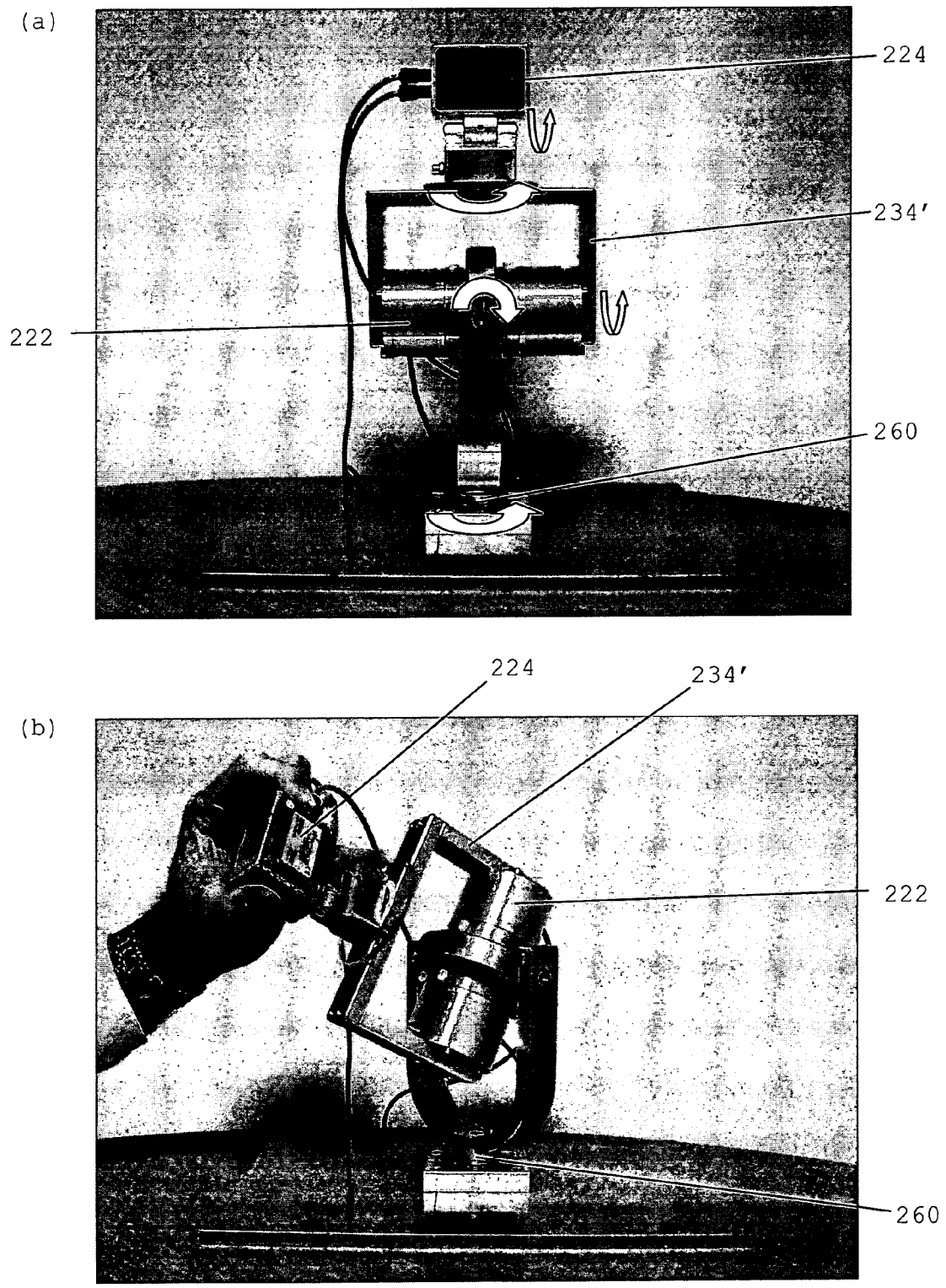
FIGS. 10*a* and *b* are images of a working prototype of a further controller according to the present invention.

A further embodiment of the controller is shown in more detail in FIGS. 10a and b, which are images of a working prototype of the controller. The further embodiment is similar to the embodiment of FIGS. 8 and 9, but differs by allowing additional rotation of body 222 about pivot 260. Less significantly, rod 234 of the embodiment of FIGS. 8 and 9 is replaced by a yoke structure 234'.

The additional rotation about pivot 260 duplicates some of the motion about rotation axis 40 and tilt axis 42, but makes it easier to reach all parts of the hemispherical surface constraint surface. To avoid the risk that trailing wires from the handle 224 become wrapped around the controller during its use, a restriction on the rotation about pivot axis 260 can be introduced. A 90° restriction has been found to work in practice. Alternatively, a wireless mechanism can be used to transmit data from the orientation sensor in handle 224.

The interrogation plane may be an interrogation surface which is not planar. For example, the interrogation plane and the interrogation window may be curved so as to match the general shape of a particular anatomic feature such as e.g. a human heart.

A controller according to the present invention may also include servos enabling the handle to be returned to a predetermined position. For example, whilst interrogating the volumetric data (or a subject's body in e.g. real-time MRI or CT), a user may come across a particular sectional view of interest, and the computer may be configured to allow the user to "bookmark" this sectional image. In essence the computer would record the mutual arrangement of the interrogation plane and the reference surface with respect to the volumetric data. Therefore, if this sectional image is lost or replaced on the display viewed by the user, the user can simply instruct the computer to re-display the sectional image. However, in addition to re-displaying the sectional image the controller 1 is returned by the servo(s) to the arrangement corresponding to the arrangement of the interrogation plane and reference surface which results in the particular sectional image.

Where the reference surface is movable with respect to the volumetric data, it is preferred that a further controller (not shown) is provided. The further controller may be a simple joystick which allows the reference surface to be moved, e.g. in 1, 2 or 3 dimensions, with respect to the volumetric data. The further controller may be rendered ineffective when each controller 1, 100 is being used to move the interrogation plane and window. However, the further controller may be able to move the reference surface when each controller 1, 100 is being used, whilst retaining the overall advantage of the present invention that the user can maintain a focus on the displayed sectional images during navigation of the interrogation window through the volumetric data.

Whilst it is envisaged that the present invention will usually be employed together with a display for displaying to a user the sectional images, the display may not be an essential feature of the invention.

Sensors other than magnetic field sensors may be used as orientation sensors to arrive at the present invention. It is conceivable that optical sensors, or even mechanical sensors could be used.

Also, whilst it is believed that the present invention is particularly suited to the interrogation of MRI and X-ray CT acquired volumetric image data to investigate multiple arbitrary planes to confirm normality or abnormality of a body (the planes are arbitrary because typically it is not known in advance which planes need to be investigated due to variations in the internal anatomy between subjects), the present invention may not be limited to such. For example, the present invention may be suited to the interrogation of geological 3D data sets.

Indeed, whilst the present invention is particularly suited to the investigation of 3D data sets, the present invention is also suited to the control of imaging systems in real-time as discussed above.

The scale of the reference surface may also be variable with respect to the constraint surface, e.g. to permit a small portion of the volumetric data to be interrogated in more detail and more easily. The reference surface may also be responsive to movement of at least portions of the volumetric data set so as to provide the user with a substantially spatially invariant image. For example, where the present invention is used in real-time MRI investigations, the reference surface may be "anchored" to particular features of e.g. the lungs of a subject's body so that the reference surface remains anchored to those points during respiration of the subject.

Of course, the method and the controller of the present invention are applicable to any system including a processor for performing the method. Indeed, the present invention is particularly suited for use in MRI or CT, and is therefore ultimately suitable for use in any MRI or CT system.

The present invention has been described with reference to preferred embodiments. Modifications of these embodiments, further embodiments and modifications thereof will be apparent to the skilled person and as such are within the scope of the invention.

The invention claimed is:

1. A computer implemented method of interrogating volumetric data, the method comprising the steps of:
   defining a reference surface relative to the volumetric data;
   providing an interrogation window lying in a movable interrogation plane intersecting the reference surface and the interrogation window intersecting the volumetric data, wherein translation and/or rotation of the interrogation plane provides a corresponding movement of the interrogation window;

said interrogation plane being associated with a pole, which lies in the interrogation plane, about which pole said interrogation plane is rotatable, and for each movement of the interrogation plane, determining the point of intersection of said pole and said reference surface, determining the relative angle of rotation of said interrogation plane about said pole and determining the angle of inclination of said pole to said reference surface; and on the basis of said determinations, providing a sectional image through the volumetric data corresponding to the position of the interrogation window within the volumetric data, wherein said interrogation plane has two or three degrees of rotational freedom and two degrees of translational freedom such that said interrogation plane is only translatable across said reference surface.

2. The computer implemented method according to claim 1, wherein the reference surface is immovable relative to the volumetric data during the movement of the interrogation plane.

3. The computer implemented method according to claim 2, wherein the reference surface is movable relative to the volumetric data between movements of the interrogation plane.

4. The computer implemented method according to claim 1, wherein the reference surface is planar.

5. The computer implemented method according claim 4, wherein the pole is at a constant angle to the line of intersection of the reference surface and the interrogation plane.

6. The computer implemented method according to claim 5, wherein the angle is substantially a right angle.

7. A computer implemented method according to claim 1 wherein the reference surface is curved.

8. A computer implemented method according to claim 7 wherein the pole is at a constant angle to a tangent to the reference surface at the point of intersection of the reference surface and the pole, the tangent lying in the interrogation plane.

9. A computer implemented method according to claim 7 wherein the angle between the pole and a tangent to the reference surface at the point of intersection of the reference surface and the pole, the tangent lying in the interrogation plane, is adjustable.

10. The computer implemented method according to claim 1, further comprising a step of generating the volumetric data.

11. A computer implemented method according to claim 10, wherein the volumetric data is generated by magnetic resonance imaging and/or by x-ray computerised tomography.

12. A computer system for implementing the method according to claim 1, the system comprising:
a processor for performing the steps of the method; and
a visual display for displaying said sectional image.

13. The computer system according to claim 12 further comprising:
a controller comprising a movable controller body for maneuvering in use said interrogation plane with respect to the reference surface.

14. The computer system according to claim 13, wherein the controller defines a constraint surface, the controller body being constrained such that all translational movement of the controller is across the constraint surface, which corresponds in use to said reference surface.

15. The computer system according to claim 14, wherein translating the controller body across the constraint surface results in use in a corresponding translation of the interrogation plane relative to the reference surface.

16. The computer system according to claim 13, wherein the controller body is rotatable about a rotation axis, which axis corresponds in use to said pole, whereby rotation of said controller body about said rotation axis provides in use a corresponding rotation of the interrogation plane about said pole.

17. The computer system according to claim 13, wherein the controller body is tiltable about a tilt axis corresponding in use to the line of intersection of the reference surface and the interrogation plane, whereby tilting the controller body about the tilt axis provides a corresponding change in the angle of inclination of said pole to said reference plane.

18. The computer system according to claim 12, wherein the computer system is a component of a magnetic imaging apparatus.

19. The computer system according to claim 12, wherein the computer system is a component of an X-ray computer tomography apparatus.

20. A computer implemented method of controlling an imaging system to provide a sectional image of a body, the method comprising the steps of:
defining a reference surface corresponding to a control surface having a pre-determined relationship with the body, with respect to which control surface a sectional image through a particular portion of the body is generatable by the imaging system;
providing an interrogation window lying in a movable interrogation plane intersecting the reference surface, wherein translation and/or rotation of the interrogation plane provides a corresponding movement of the interrogation window;
said interrogation plane being associated with a pole, which lies in the interrogation plane, about which pole said interrogation plane is rotatable, and for each movement of the interrogation plane, determining the point of intersection of said pole and said reference surface, determining the relative angle of rotation of said interrogation plane about said pole and determining the angle of inclination of said pole to said reference surface; and
on the basis of said pre-determined relationship and said determinations, providing a sectional image through the body, the sectional image corresponding to the relative position and orientation of the interrogation window to the reference surface,
wherein said interrogation plane has two or three degrees of rotational freedom and two degrees of translational freedom such that said interrogation plane is only translatable across said reference surface.

21. A controller comprising:
a movable controller body for maneuvering an interrogation plane with respect to a reference surface defined relative to volumetric data, said interrogation plane being associated with a pole, which lies in the interrogation plane, said interrogation plane being rotatable about said pole, and said interrogation plane intersecting the reference surface and having two or three degrees of rotational freedom and two degrees of translational freedom such that said interrogation plane is only translatable across said reference surface,
wherein said controller defines a constraint surface, and said controller body is constrained such that all translational movement of said controller is across said constraint surface, which corresponds in use to said reference surface, and wherein said controller body is rotatable about a rotation axis that lies within the controller body and corresponds to said pole about which the interrogation plane is rotatable.

* * * * *